(12) United States Patent
Freeman

(10) Patent No.: US 9,242,115 B2
(45) Date of Patent: Jan. 26, 2016

(54) COORDINATED RESUSCITATION PERFUSION SUPPORT

(71) Applicant: ZOLL Medical Corporation, Chelmsford, MA (US)

(72) Inventor: Gary A. Freeman, Newton Center, MA (US)

(73) Assignee: ZOLL MEDICAL CORPORATION, Chelmsford, MA (US)

(*) Notice: Subject to any disclaimer, the term of this patent is extended or adjusted under 35 U.S.C. 154(b) by 0 days.

(21) Appl. No.: 14/294,777

(22) Filed: Jun. 3, 2014

(65) Prior Publication Data
US 2014/0288609 A1    Sep. 25, 2014

Related U.S. Application Data

(62) Division of application No. 13/398,344, filed on Feb. 16, 2012, now Pat. No. 8,774,945.

(60) Provisional application No. 61/473,273, filed on Apr. 8, 2011.

(51) Int. Cl.
| | | |
|---|---|---|
| A61N 1/39 | (2006.01) | |
| A61N 1/362 | (2006.01) | |
| A61H 31/00 | (2006.01) | |
| A61B 5/11 | (2006.01) | |

(52) U.S. Cl.
CPC ........... *A61N 1/3987* (2013.01); *A61H 31/005* (2013.01); *A61N 1/3625* (2013.01); *A61N 1/39* (2013.01); *A61B 5/11* (2013.01); *A61H 2201/1253* (2013.01); *A61H 2201/501* (2013.01); *A61H 2201/5043* (2013.01); *A61H 2201/5071* (2013.01); *A61H 2201/5079* (2013.01); *A61H 2230/045* (2013.01); *A61H 2230/06* (2013.01); *A61H 2230/208* (2013.01); *A61H 2230/30* (2013.01); *A61H 2230/305* (2013.01)

(58) Field of Classification Search
None
See application file for complete search history.

(56) References Cited

U.S. PATENT DOCUMENTS

| | | | |
|---|---|---|---|
| 5,431,688 | A | 7/1995 | Freeman |
| 6,125,299 | A | 9/2000 | Groenke et al. |
| 6,213,960 | B1 | 4/2001 | Sherman et al. |
| 6,360,125 | B1 | 3/2002 | Weil et al. |
| 6,463,327 | B1 | 10/2002 | Lurie et al. |
| 2003/0208237 | A1 | 11/2003 | Locke et al. |
| 2004/0162510 | A1 | 8/2004 | Jayne et al. |
| 2005/0067816 | A1 | 3/2005 | Buckman |

(Continued)

FOREIGN PATENT DOCUMENTS

| | | |
|---|---|---|
| EP | 1913923 | 4/2008 |
| WO | WO 00/57955 | 10/2000 |

(Continued)

OTHER PUBLICATIONS

Invitation to Pay Additional Fees and, Where Applicable, Protest Fee, PCT/US2012/025358, mailed Sep. 25, 2012, 7 pages.

(Continued)

*Primary Examiner* — Brian T Gedeon
*Assistant Examiner* — Ankit Tejani
(74) *Attorney, Agent, or Firm* — The Webb Law Firm

(57) ABSTRACT

This document relates to systems and techniques for the treatment of a cardiac arrest victim via electromagnetic stimulation of physiologic tissue.

22 Claims, 8 Drawing Sheets

(56) References Cited

U.S. PATENT DOCUMENTS

| | | |
|---|---|---|
| 2005/0119706 A1 | 6/2005 | Ideker et al. |
| 2005/0234515 A1 | 10/2005 | Freeman |
| 2007/0060785 A1 | 3/2007 | Freeman et al. |
| 2008/0081321 A1 | 4/2008 | Cantrell et al. |
| 2008/0300518 A1 | 12/2008 | Bowes |
| 2008/0312565 A1 | 12/2008 | Celik-Butler et al. |
| 2009/0112274 A1 | 4/2009 | Herbert |
| 2010/0222718 A1* | 9/2010 | Freeman ............. A61H 31/00 601/41 |
| 2011/0313482 A1 | 12/2011 | Dupelle et al. |

FOREIGN PATENT DOCUMENTS

| | | |
|---|---|---|
| WO | WO 2005/021089 | 3/2005 |
| WO | WO 2005/070497 | 8/2005 |
| WO | WO 2006/058133 | 6/2006 |
| WO | WO 2006/104977 | 10/2006 |
| WO | WO 2010/010567 | 1/2010 |

OTHER PUBLICATIONS

Invitation to Pay Additional Fees and, Where Applicable, Protest Fee, PCT/US2012/025401, mailed Sep. 25, 2012, 7 pages.

International Search Report & Written Opinion, PCT/US2012/025358, mailed Nov. 22, 2013, 23 pages.

* cited by examiner

COORDINATED RESUSCITATION PERFUSION SUPPORT

CROSS-REFERENCE TO RELATED APPLICATIONS

This application is a divisional of and claims priority under 35 U.S.C. §120 to U.S. application Ser. No. 13/398,344, filed on Feb. 16, 2012, now U.S. Pat. No. 8,774,945, issued on Jul. 8, 2014, which claims benefit of priority under 35 U.S.C. §119 to U.S. Application Ser. No. 61/473,273 filed Apr. 8, 2011. All subject matter set forth in the above referenced application is hereby incorporated by reference into the present application as if fully set forth herein.

TECHNICAL FIELD

This document relates to systems and techniques for the treatment of a cardiac arrest victim via electromagnetic stimulation of physiologic tissue.

BACKGROUND

Cardiac Arrest, or Sudden Death, is a descriptor for a diverse collection of physiological abnormalities with a common cardiac etiology, wherein the patient typically presents with the symptoms of pulselessness, apnea and unconsciousness. Cardiac arrest is widespread, with an estimated 300,000 victims annually in the U.S. alone and a similar estimate of additional victims worldwide. Early defibrillation is the major factor in sudden cardiac arrest survival. There are, in fact, very few cases of cardiac arrest victims saved which were not treated with defibrillation. There are many different classes of abnormal electrocardiographic (ECG) rhythms, some of which are treatable with defibrillation and some of which are not. The standard terminology for this is "shockable" and "non-shockable" ECG rhythms, respectively. Non-shockable ECG rhythms are further classified into hemodynamically stable and hemodynamically unstable rhythms. Hemodynamically unstable rhythms are those which are incapable of supporting a patient's survival with adequate blood flow (non-viable). For example, a normal sinus rhythm is considered non-shockable and is hemodynamically stable (viable). Some common ECG rhythms encountered during cardiac arrest that are both non-shockable and hemodynamically unstable are: bradycardia, idioventricular rhythms, pulseless electrical activity (PEA) and asystole. Bradycardias, during which the heart beats too slowly, are non-shockable and also possibly non-viable. If the patient is unconscious during bradycardia, it can be helpful to perform chest compressions until pacing becomes available. Idioventricular rhythms, in which the electrical activity that initiates myocardial contraction occurs in the ventricles but not the atria, can also be non-shockable and non-viable (usually, electrical patterns begin in the atria). Idioventricular rhythms typically result in slow heart rhythms of 30 or 40 beats per minute, often causing the patient to lose consciousness. The slow heart rhythm occurs because the ventricles ordinarily respond to the activity of the atria, but when the atria stop their electrical activity, a slower, backup rhythm occurs in the ventricles. Pulseless Electrical Activity (PEA), the result of electro-mechanical dissociation (EMD), in which there is the presence of rhythmic electrical activity in the heart but the absence of myocardial contractility, is non-shockable and non-viable and would require chest compressions as a first response. Asystole, in which there is neither electrical nor mechanical activity in the heart, cannot be successfully treated with defibrillation, as is also the case for the other non-shockable, non-viable rhythms. Pacing is recommended for asystole, and there are other treatment modalities that an advanced life support team can perform to assist such patients, e.g. intubation and drugs. The primary examples of shockable rhythms that can be successfully treated with defibrillation are ventricular fibrillation, ventricular tachycardia, and ventricular flutter.

Normally, electrochemical activity within a human heart causes the organ's muscle fibers to contract and relax in a synchronized manner. This synchronized action of the heart's musculature results in the effective pumping of blood from the ventricles to the body's vital organs. In the case of ventricular fibrillation (VF), however, abnormal electrical activity within the heart causes the individual muscle fibers to contract in an unsynchronized and chaotic way. As a result of this loss of synchronization, the heart loses its ability to effectively pump blood. Defibrillators produce a large current pulse that disrupts the chaotic electrical activity of the heart associated with ventricular fibrillation and provides the heart's electrochemical system with the opportunity to re-synchronize itself. Once organized electrical activity is restored, synchronized muscle contractions usually follow, leading to the restoration of effective cardiac pumping.

With the first clinical use in humans described in 1956 by Dr. Paul Zoll, transthoracic defibrillation has become the primary therapy for cardiac arrest, ventricular tachycardia (VT), and atrial fibrillation (AF). Monophasic waveforms dominated until 1996, when the first biphasic waveform became available for clinical use. Actual survival-to-hospital-discharge rates remain an abysmal ten percent or less. Survival rates from cardiac arrest remain as low as 1-3% in major U.S. cities, including those with extensive, advanced pre-hospital medical care infrastructures.

The importance of good quality, deep compressions on improving survival has recently been rediscovered by the clinical community. The American Heart Association, in their most recent 2010 Guidelines, state, "The scientists and healthcare providers participating in a comprehensive evidence evaluation process analyzed the sequence and priorities of the steps of CPR in light of current scientific advances to identify factors with the greatest potential impact on survival. On the basis of the strength of the available evidence, they developed recommendations to support the interventions that showed the most promise. There was unanimous support for continued emphasis on high-quality CPR, with compressions of adequate rate and depth, allowing complete chest recoil, minimizing interruptions in chest compressions and avoiding excessive ventilation."

In spite of the recommendations from the AHA and other recognized clinical bodies that good quality compressions with no pausing is important for cardiac arrest survival, compressions without pauses is actually very difficult to achieve, even with clinical use protocols that are specifically designed to achieve continuous compressions, with no ventilation pauses. It has been shown that CPR fraction, the percentage of time during the course of resuscitation during which compressions are present, is only 60-70% even for those systems which utilize the continuous compression approach to eliminate the ventilation pauses. The CPR fraction can be further increased to 80-85% when defibrillators are utilized that incorporate a motion sensor under the rescuers hands and provide real time feedback to the rescuer on the quality of their compressions (RealCPRHelp, ZOLL Medical, Chelmsford).

Devices for augmentation of circulation by pacing of asystole and bradycardia combined with defibrillation have been available for a number of years. U.S. Pat. No. 4,088,138 describes a device that automatically paces a patient either before or after a defibrillation shock when either profound bradycardia or asystole is detected.

Use of electrical stimulation of skeletal muscles to deliver blood flow similar to conventional sternal chest compressions during CPR has been described by Wang and colleagues in Crit Care Med 2008; 36[Suppl.]:S458-S466. As the authors note, however, the method is of limited value as skeletal muscle fatigue onset is fairly rapid, even under optimal lab conditions; fatigue onset was found to be less than one minute in most cases. It should be noted that a typical clinically advised interval for chest compressions is two minutes, thus efficacious stimulation will not reliably be achieved for even one full CPR interval. The technique is further elucidated, for example, in U.S. Pat. Nos. 5,782,883, 6,185,457, 5,978,703, 6,314,319, and 6,567,607.

There are two primary mechanisms for generation of blood flow during chest compression in cardiopulmonary resuscitation (CPR): the cardiac pump mechanism and the thoracic pump mechanism. "The cardiac pump hypothesis holds that blood flow is generated during closed-chest compressions when the heart is squeezed between the sternum and the vertebral column. This mechanism of flow implies that ventricular compression causes closure of the atrioventricular valves and that ejection of blood reduces ventricular volume. During chest relaxation, ventricular pressure falls below atrial pressure, allowing the atrioventricular valves to open and the ventricles to fill. This sequence of events resembles the normal cardiac cycle and occurs during cardiac compression when open-chest CPR is used." [Peter Trinkaus, Charles L. Schleien, Physiologic Foundations of Cardiopulmonary Resuscitation, In: Bradley P. Fuhrman, MD, and Jerry J. Zimmerman, MD, PhD, Editor(s), Pediatric Critical Care (Third Edition), Mosby, Philadelphia, 2006, Pages 1795-1823, ISBN 978-0-32-301808-1, DOI: 10.1016/B978-032301808-1.50121-8.] Trinkaus goes on to say, "During normal cardiac function, the lowest pressure in the vascular circuit occurs on the atrial side of the atrioventricular valves. This low pressure compartment is the downstream pressure for the systemic circulation, which allows venous return to the heart. Angiographic studies show that blood passes from the venae cavae through the right heart into the pulmonary artery and from the pulmonary veins through the left heart into the aorta during a single chest compression. Echocardiographic studies show that, unlike normal cardiac activity or during open chest CPR, during closed-chest CPR in both dogs and humans the atrioventricular valves are open during blood ejection and aortic diameter decreases rather than increases during blood ejection. These findings during closed-chest CPR support the thoracic pump theory and argue that the heart is a passive conduit for blood flow." (FIG. 1). In practice, the mechanism of blood flow generation during chest compressions is both cardiac and thoracic, with the relative proportion of effect being a function of the patient's individual vascular and valvular state as well as the performance parameters of the chest compression, particularly with regard to the depth, rate and release of the compression.

A typical patient will require approximately 100-200 pounds of force for the rescuer to compress the sternum to the recommended depth of 2 inches. The guidelines further recommend that the rate of compressions be at one compression every 600 milliseconds. During a normal resuscitation, as a result of this level of exertion, the rescuer responsible for performing chest compressions will fatigue from the effort even in as short a time as one minute. In response to the fatigue, the rescuer will respond by either switching roles with another rescuer, by pausing compressions, or by reducing their level of exertion which will inevitably result in insufficient compression effectiveness. In the case of switching rescuers, this procedure will result in pauses in compressions of at least 10 seconds and potentially 30 seconds if the action is performed inefficiently. During this period of pausing, the patient is of course not receiving the life-saving therapy of chest compressions, and no blood is being delivered to the heart, brain and other vital organs. It would thus be desirable to have an automatic means of delivering perfusion during periods of switching rescuers, periods of rescuer fatigue, pauses and other lapses in compression quality.

Attempts to use electrical stimulation for ventilation during CPR have also been described in U.S. Pat. No. 6,213,960 for electrostimulation in conjunction with a chest compression device and stimulation of nerves controlling ventilation. U.S. Pat. Nos. 6,463,327 and 6,234,985 also describe the use diaphragmatic stimulation by the phrenic nerve in order to augment venous return and hemodynamics during CPR. The use of phrenic stimulation for cardiac arrest victims has not been found to be particularly effective for several reasons: 1) the patient has been anoxic for an extended period during cardiac arrest prior to treatment, resulting in degraded metabolic status of the whole nervous system, including the phrenic nerve, making electrostimulation much less effective than with conscious patients; 2) non-invasive locations for stimulation electrodes on the thorax also stimulate the intercostal muscles that cause exhalation, in direct opposition to the inspiratory effect caused by phrenic stimulation and its associated diaphragmatic contraction; and 3) while the phrenic nerve in the neck can be stimulated non-invasively, is often difficult to locate, particularly in the pre-hospital environment and under the acute, emergent situation of cardiac arrest.

SUMMARY

This document describes systems and techniques that may be used to provide improved chest compression for a patient or victim who is suffering from ventricular fibrillation or a similar malady.

In some aspects, a medical system for providing electromagnetic stimulation of a patient includes a sensor positioned to sense the presence of manual chest compressions administered to the patient by a rescuer. The system also includes a processor arranged to receive data generated by the sensor and detect changes in the administration of the chest compressions and circuitry configured for delivery of electromagnetic stimulation to the patient to stimulate blood flow in the patient upon detection of the change in the administration of the chest compressions.

Embodiments can include one or more of the following.

The changes can include a degradation in the quality of the chest compressions.

The degradation in the quality of the chest compressions can include a change in depth of the chest compressions.

The degradation in the quality of the chest compressions can include a change in compression release of the chest compressions.

The processor can be configured to detect changes in the administration of the chest compressions by detecting an absence of chest compressions for a period of time greater than a threshold.

The processor can be configured to detect changes in the administration of the chest compressions by detecting an absence of chest compressions for a period of time greater than a 2 seconds.

The processor can be configured to detect changes in the administration of the chest compressions by comparing data generated by the sensor during a first time period with data generated by the sensor during a second time period that occurs after the first time period.

The sensor can be configured to detect motion of the patient's sternum.

The sensor can include a motion sensor, a pressure sensor, and/or a velocity sensor.

The circuitry configured for delivery of electromagnetic stimulation can be further configured to deliver the electromagnetic stimulation automatically and without user intervention.

The circuitry configured for delivery of electromagnetic stimulation can include an electrode assembly affixed to the patient's thorax.

The electrode assembly can be removably affixed to the patient's thorax.

The circuitry can include circuitry configured to deliver a pulse packet of 100-200 microsecond duration pulses with inter-pulse spacing of 5-15 milliseconds and an amplitude of 300-700 volts.

The circuitry can include circuitry configured to deliver a pulse packet of 20-1000 microsecond duration pulses with a duty cycle of 2-95% and an amplitude of 50-2000 volts.

The system can also include a display device configured to visually prompt the rescuer to resume manual chest compressions upon initiation of delivery of the electromagnetic stimulation to the patient.

The system can also include a speaker configured to provide an audio prompt the rescuer to resume manual chest compressions upon initiation of delivery of the electromagnetic stimulation to the patient.

The processor can be configured to detect changes in the administration of the chest compressions by detecting a degradation in the quality of chest compressions.

The circuitry can be configured to deliver the electromagnetic stimulation simultaneously with the administration of the manual chest compressions by the rescuer upon detection of the degradation in the quality of chest compressions.

In some additional aspects, an external defibrillator for providing controlled shock to victims of heart problems includes an electrical storage device capable of delivering a defibrillating shock to a patient. The defibrillator also includes a proximity sensor configured to determine a location of the rescuer's hands relative to the patient and a controller programmed to calibrate the proximity sensor by analyzing data from the proximity sensor received during a time period corresponding to delivery manual administration of chest compressions by the rescuer and to cause the electrical storage device to deliver a defibrillating shock to the patient based at least in part on data from the proximity sensor.

Embodiments can include one or more of the following.

The proximity sensor can be a capacitance sensor.

The proximity sensor can be further configured to detect removal of the rescuer's hands from the patient.

The controller can be further configured to cause the electrical storage device to deliver a defibrillating shock to the patient upon detecting the rescuer is at least two inches away from the patient.

The proximity sensor can be an ultrasonic sensor.

The proximity sensor can be a light emitter-receiver pair.

In some additional aspects, a medical system for providing electromagnetic stimulation of a patient can include a first set of electrodes configured to be located to initiate blood flow based on a cardiac pump mechanism and a second of electrodes configured to be located to initiate blood flow based on a thoracic pump mechanism. The system can also include a controller programmed sequence delivery of electrical energy from the first set of electrodes and the second set of electrodes to generate dual-stage electrical stimulation configured to cause blood flow in the patient.

Embodiments can include one or more of the following.

The dual-stage electrical stimulation can include a first stage during which the controller is configured to activate the first set of electrodes and a second stage during which the controller is configured to activate the second set of electrodes.

The second set of electrodes can be configured to be positioned at locations that primarily stimulate thoracic muscle groups that during contraction produce blood flow primarily via the thoracic pump mechanism.

The second set of electrodes can be configured to be positioned on the left and right sides of the patient at the bottom of the rib cage.

The controller can be further programmed sequence delivery of electrical energy from the first set of electrodes and the second set of electrodes by delivering a pulse from the second set of electrodes 100-500 milliseconds after delivering a pulse from the first set of electrodes.

The controller can be further programmed sequence delivery of electrical energy from the first set of electrodes and the second set of electrodes by delivering a pulse from the second set of electrodes 100-200 milliseconds after delivering a pulse from the first set of electrodes.

In some additional aspects, a method for promoting sternocostal inhalation includes electrically stimulating a first set muscles that attach to some portion of the ribs and electrically stimulating a second set of muscles that when contracted cause an opposing motion of the spine.

Embodiments can include one or more of the following.

Electrically stimulating the second set of muscles can cause an opposing motion of the spine in either the sagittal or transverse axis.

Electrically stimulating the first set muscles can include electrically stimulating the first set muscles using a first cathodal electrode located above the right rhomboid major muscle and a second cathodal electrode located above the left rhomboid major.

Electrically stimulating the first set muscles further can include electrically stimulating the first set muscles using an anodal electrodes located above the scapula.

Electrically stimulating the second set of muscles can include electrically stimulating the second set of muscles using a first cathodal electrode located above the left serratus anterior muscle and a second cathodal electrode located above the right serratus anterior muscle.

Electrically stimulating the second set of muscles can include electrically stimulating the second set of muscles at a time subsequent to electrically stimulating the first set muscles.

Electrically stimulating the first and second sets of muscles can include electrically stimulating the first and second sets of muscles during an upstroke of a manual chest compression.

Electrically stimulating the first and second sets of muscles can include electrically stimulating the first and second sets of muscles using a pulse width modulated waveform.

Electrically stimulating the first and second sets of muscles can include electrically stimulating the first and second sets of muscles using a waveform comprising a ramped leading edge.

DETAILED DESCRIPTION

This document describes mechanisms by which chest compressions for a patient suffering from sudden cardiac arrest can be coordinated with electromagnetic stimulation of various locations on the patient's thorax.

Good quality compressions with little or no pausing (e.g., substantially continuous administration of compressions) are important for cardiac arrest survival. However, it is difficult for the average rescuer to provide continuous, high quality manual compressions without pauses. Systems and methods are described herein to automatically detect the cessation or pausing of a rescuer's manual administration of chest compressions and supplement the treatment of the patient with electrical stimulation during the time periods of such pauses. The electrical stimulation begins automatically based on detected characteristics related to the manual administration of chest compressions such that the time period between cessation or pausing of the manual chest compressions and administration of the electrical stimulation is brief (e.g., less than 10 seconds, less than 5 seconds, less than 3 seconds). Examples of such electrical stimulation include electrical stimulation of skeletal muscles to deliver blood flow similar to conventional sternal chest compressions during CPR and two-stage stimulation to sequentially apply electrical stimulation to encourage circulation based on the cardiac pump mechanism and thoracic pump mechanism both of which are described in more detail below.

Due to the rapid onset of skeletal muscle fatigue which reduces the utility of the electrical stimulation, the period of time that the blood flow is stimulated by the application of electrical stimulation limited (e.g., less than one minute, less than 30 seconds). In order to encourage the rescuer to resume manual chest compressions, the system can provide visual and/or audio prompts to the rescuer instructing the rescuer to resume manual chest compressions shortly after beginning electrical stimulation (e.g., 5 seconds after detection of cessation of effective compressions or beginning electrical stimulation, 10 seconds after detection of cessation of effective compressions or beginning electrical stimulation, 20 seconds after detection of cessation of effective compressions or beginning electrical stimulation).

Figure 1:
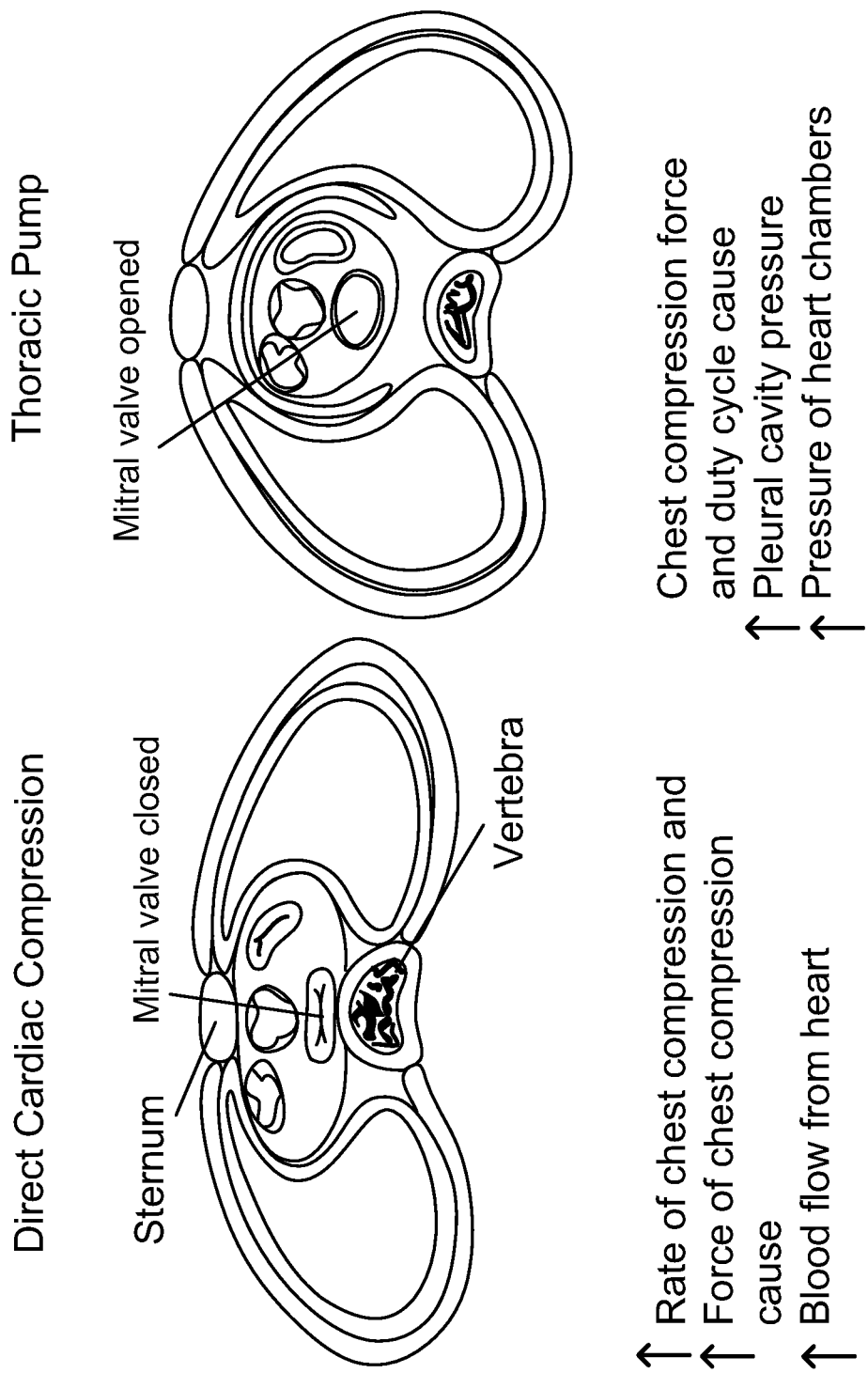
FIG. 1 shows the two primary modes of blood flow during CPR.
Figure 2B:
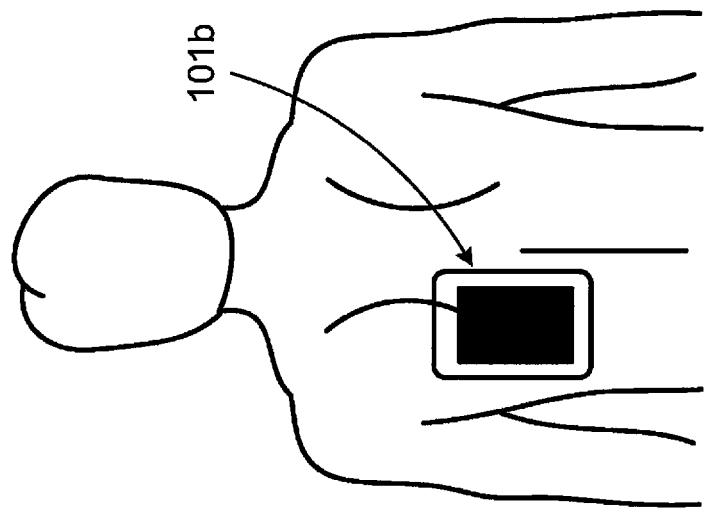
FIGS. 2a and 2b shows anterior and posterior electrode assemblies, respectively, applied to a patient.
Figure 2A:
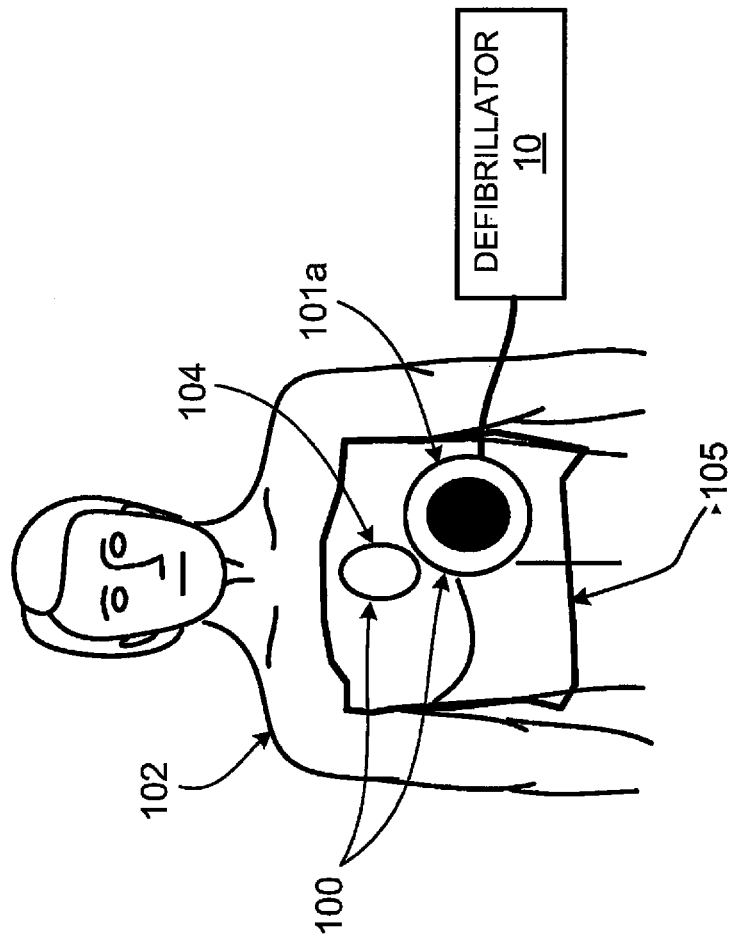

In some examples, the electrical stimulation can be administered by, for example, an anterior electrode assembly (AEA) 100 affixed to the patient's 102 thorax as described in relation to FIGS. 2A and 2B below. FIGS. 2A and 2B show anterior and posterior electrode assemblies, respectively, applied to a patient.

Figure 3:
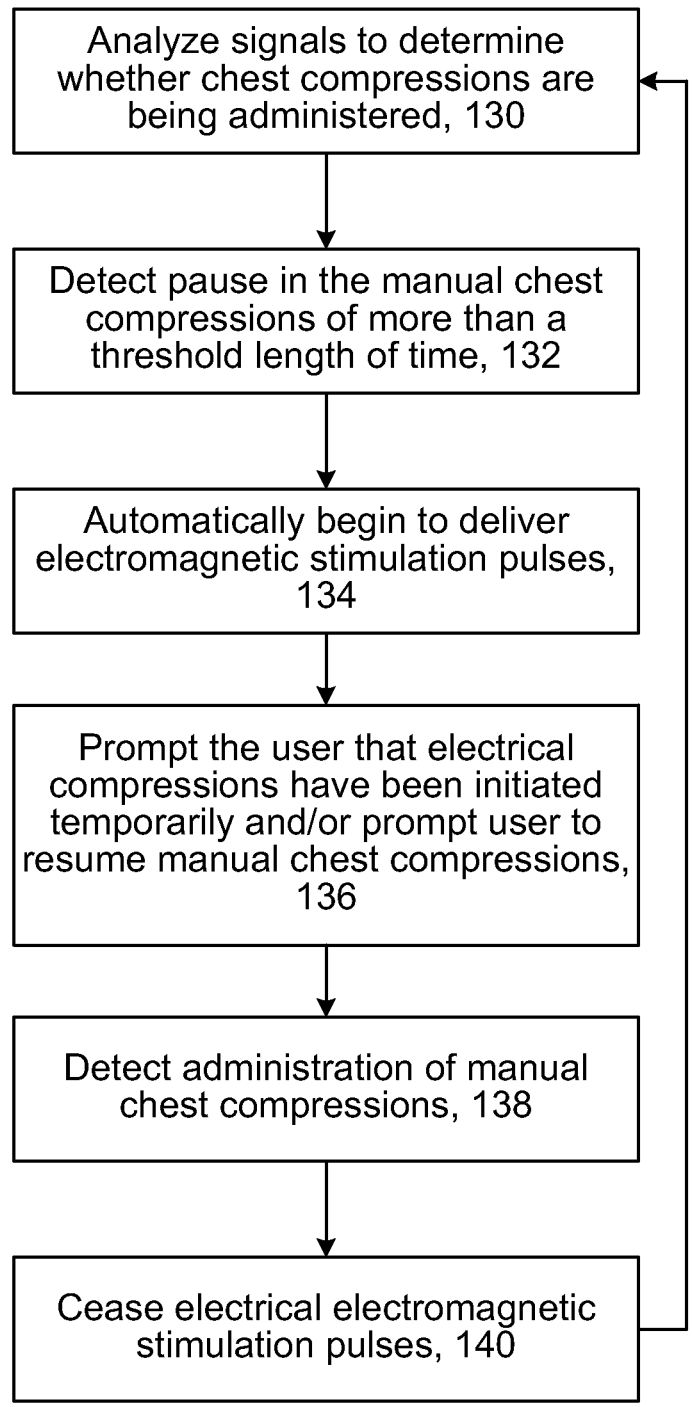
FIG. 3 is a flow chart of a method for generating electromagnetic stimulation pulses.

The AEA 100 is composed of a defibrillation/pacing/monitoring electrode 101 known to those skilled in the art, composed of a conductive adhesive gel in contact with the patient's skin, typically also a conductive metallic surface on the conductive gel for distributing the current delivered by the stimulation device, and an insulative top layer. Thus, the AEA 100 can be removably affixed to the patient's thorax. A housing 104 containing a motion sensor along with power and signal conditioning electronics is positioned on the patient's sternum, and is used to measure the motion of the sternum during CPR chest compressions. The motion sensor may be an accelerometer as is used commercially in devices of this type (ZOLL CPR STAT-PADZ®, Chelmsford, Mass.) or may be a pressure sensor, a velocity sensor such as those employing a time-varying magnetic flux and coil arrangement or other varied motion sensors. Defibrillator 10 processes conditioned motion sensor signal via the Sternal Motion analysis subsystem to determine when the rescuer has ceased chest compressions, paused in the administration of chest compressions, or is no longer administering effective chest compressions. The Sternal Motion analysis subsystem can be, for example, a software function that is part of the software code for running the Defibrillator 10 in general, or may be specialized hardware either in the defibrillator or in the housing 104 that may communicate to the defibrillator Microprocessor via, for instance, a serial communication channel such as USB™, RS232 or BLUETOOTH®. During the course of any typical CPR interval, the duration of which is typically on the order of 2 minutes, a rescuer may stop briefly at multiple points, sometimes for as little as 3-10 seconds. Each of these pauses has a significant adverse impact on the potential of the patient to achieve return of spontaneous circulation (ROSC) during the course of the resuscitation attempt. Referring now to FIG. 3, the microprocessor analyzes signals to determine when the rescuer has paused or ceased chest compressions (130). When the Microprocessor detects a pause in the manual chest compressions of more than a threshold length of time (132), for example, more than about 2 seconds, more than about 3 seconds, more than about 5 seconds, the system will automatically begin to deliver electromagnetic stimulation pulses via the electrodes 101 and 101b (134). In animal testing it was found that the optimal stimulation waveform was a pulse packet of 100-200 microsecond duration pulses with inter-pulse spacing of 10 milliseconds and a train length of 5-10 pulses and an amplitude of approximately 500 Volts. At the same time that electromagnetic perfusion stimulation (EPS) is initiated, the defibrillator begins prompting the user that electrical compressions have been initiated temporarily and/or to prompting the user to resume manual chest compressions (136). The prompting may be either visual text on the display screen of the defibrillator or in the form of speech prompts. The duration of the EPS will be limited to some period of time typically not to exceed 1 minute, though at minimum, the EPS duration may be limited to as short a time period as 5-10 seconds. A period of approximately 15 seconds will be particularly helpful when the rescuer performing compressions has fatigued and the rescuers are switching roles, or when the rescuer performing compressions is pausing due either to fatigue or being distracted by some event in the rescue environment, an alarm on the defibrillator or having to perform a function like endotracheal intubation. The system continues to monitor the signals to determine when the rescuer resumes manual chest compressions. Upon detection that the rescuer has resumed manual chest compressions (138), the system ceases providing the electrical compressions (140) and resumes monitoring the quality of the manual chest compressions (130).

By analyzing the compression characteristics, it is possible to determine whether or not the rescuer is fatigued. For example, in the example provided above, the system can detect fatigue based on a degradation of the quality of chest compressions in addition to or instead of detecting the complete cessation of administration of chest compressions and administer electrical stimulations based on the detection of such changes in the chest compression quality. Generally, methods for detecting fatigue can include determining initial statistical characteristics of the rescuer's compressions, and then analyzing the compression characteristics for any significant, sustained degradations. For instance, the known techniques such as change point analysis such as that described by Basseville (Basseville M, Nikiforov I V. Detection of Abrupt Changes: Theory and Application. Engelwood, N.J.: Prentice-Hall 1993) or Pettitt (Pettitt A N. A simple cumulative sum type statistic for the change point problem with zero-one observations. Biometrika 1980; 67:79-84.) Other known methods such as Shewhart control charts may be employed for first detecting changes in the characteristics and then assessing whether the change detected is both a degradation and of a sufficient magnitude to cause the defibrillator to first initiate prompts to improve that particular aspect of the compression characteristic and then if the quality does not improve sufficiently then initiate temporary EPS as a stop-gap measure and deliver a prompt to switch rescuers.

In some embodiments, the EPS may be delivered substantially simultaneous to the manual compressions delivered by the rescuer, particularly in the case where the compression are still ongoing, but are of diminished quality. In order to prevent electrical shock to the rescuer, the sensor housing 104 and electrode 101 may be integrated into a thin, flexible dielectric insulative sheet 105. Mylar plastic may be used for such a material, preferably of about 0.5 mil thickness.

In some embodiments, the sensor housing and electrodes are configured to ensure that the rescuer's hands have been removed from the patient (e.g., are not in contact with the patient) prior to administration of a defibrillation shock and or delivery the electrical stimulations for electrical compressions. For example, the sensor housing can include a proximity sensor (e.g., a capacitance sensor) that determines whether a rescuer is in contact with the patient and prohibits delivery of electrical current to the patient when the rescuer is in contact with the patient. In some additional examples, as described in more detail below, the system can be configured to coordinate the delivery of the defibrillation shock with the detection that the rescuer has removed his/her hands from the patient. For example, the defibrillation shock can be delivered automatically and without requiring further user action upon detection that the rescuer has removed his/her hands from the patient.

Figure 7:
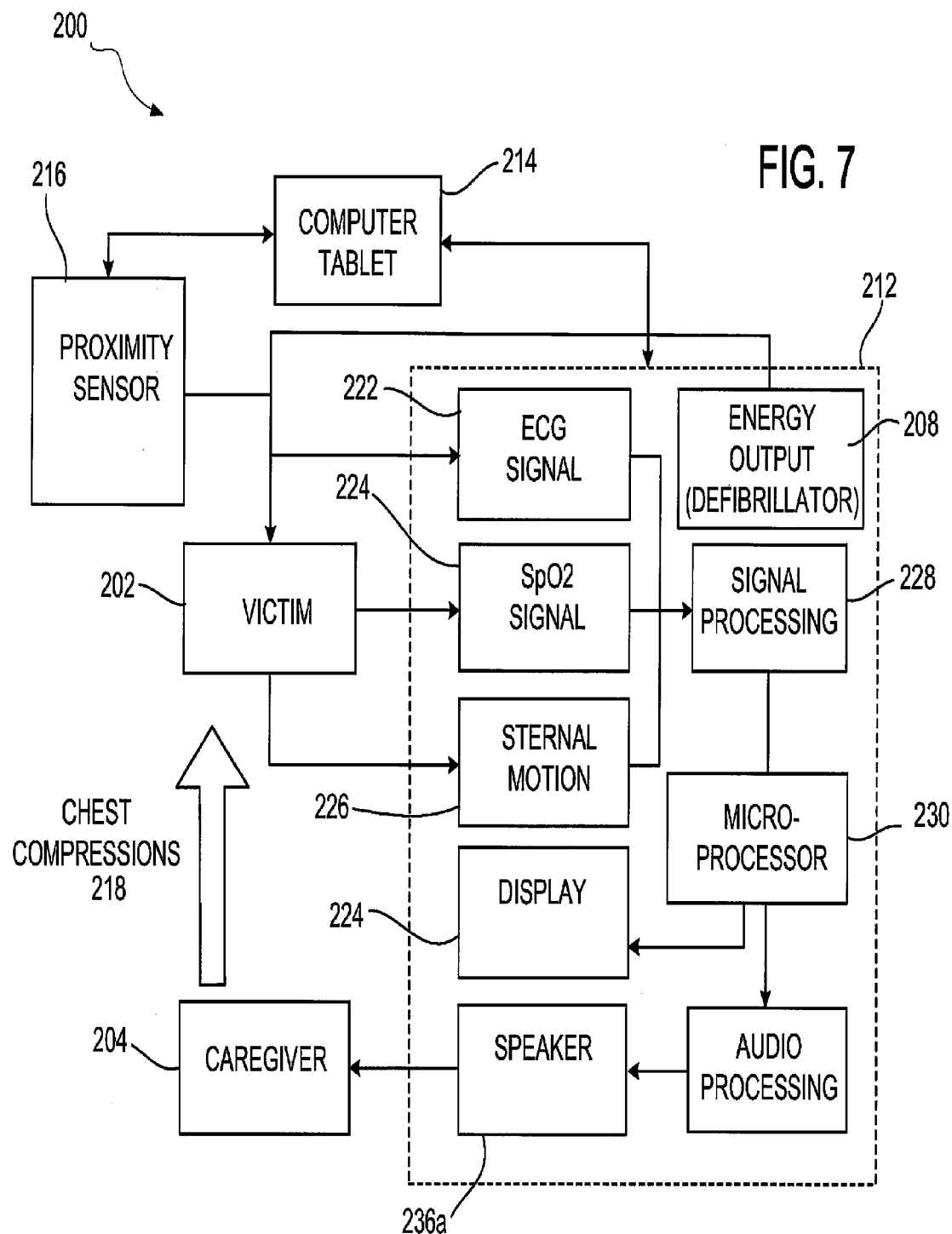
FIG. 7 is a block diagram of the system.
Figure 8:
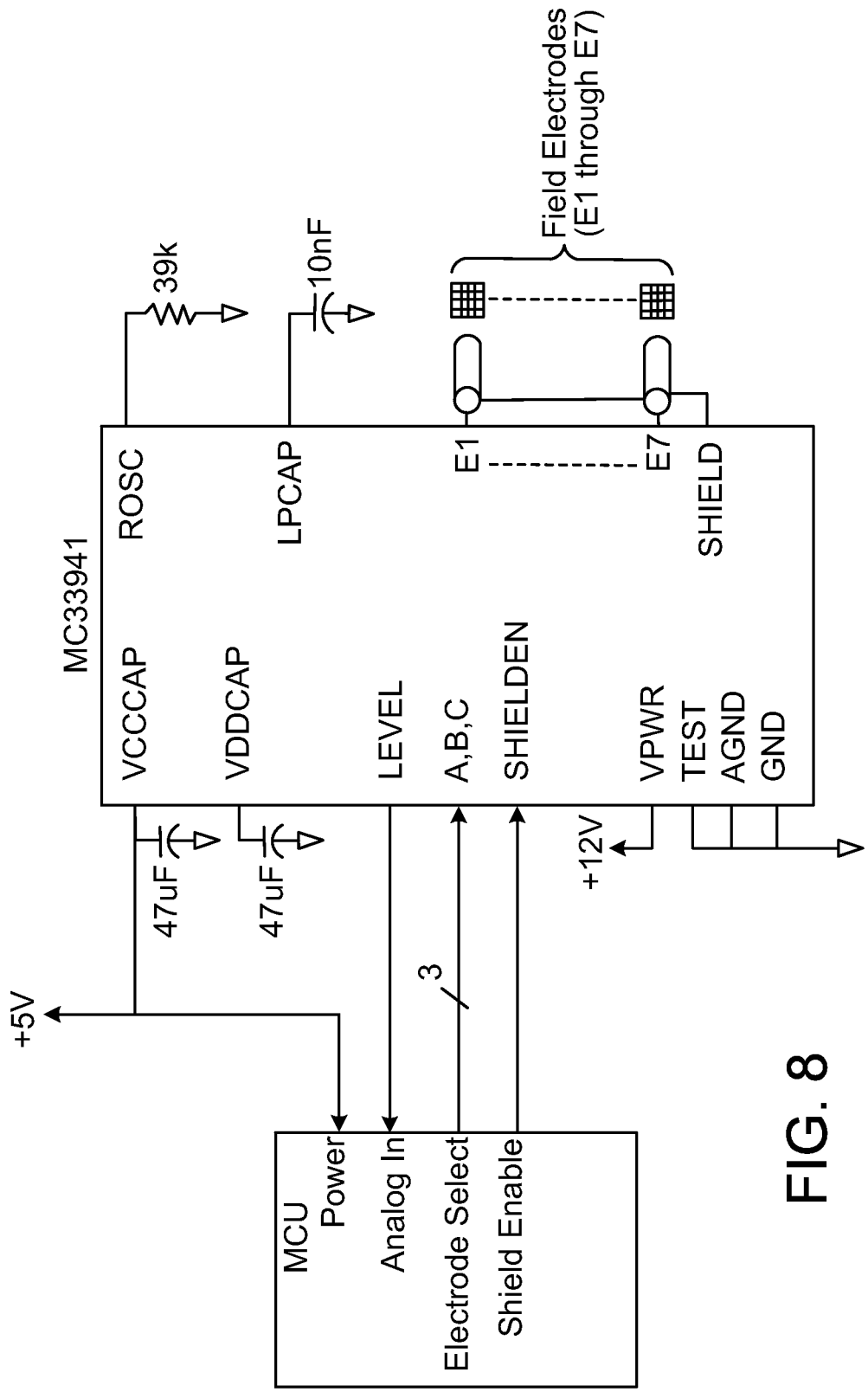
FIG. 8 shows a schematic for an E-field proximity sensor 216.

More particularly, the sensor housing 104 may also contain a proximity sensor 216 for measuring the location of the rescuer's hands (e.g., as shown in FIGS. 7 and 8). This measurement of rescuer hand location may be used in several possible ways. In cases where the electrode assembly AEA 100 does not incorporate an insulative sheet 105, the hand location measurement may be used to hold off EPS (e.g., prohibit delivery of electrical pulses) until the rescuer has removed their hands from the patient's chest. Additionally, upon detection of fatigue or cessation of manual chest compressions, the device can provide audio and/or visual prompting to the rescuer instructing them to remove their hands from patient's chest until such time as they do remove their hands. The hand measurement may also be used as a triggering mechanism for delivery of therapeutic electromagnetic energy (e.g., defibrillation shock) to the patient. It is believed that automatically delivering the therapeutic electromagnetic energy upon detection of the removal of the rescuer's hands can reduce the time between cessation of manual chest compressions and delivery of the therapeutic electromagnetic energy. For example, the defibrillator may be charged during delivery of the manual chest compressions such that the therapeutic electromagnetic energy can be delivered immediately (e.g., within less than 1 second) after the cessation of manual chest compressions.

Without the automatic detection of the removal of the rescuer's hands and using the detection to trigger the delivery of the therapeutic electromagnetic energy, when treating a patient who has a shockable rhythm, the defibrillator may be charged by a second rescuer while the first delivers ongoing compressions. At the moment for delivering a shock, however, the first rescuer controlling the defibrillator will have the rescuer delivering stop compressions until after the shock is delivered by the first rescuer. This involves a set of clearance commands between the two rescuers, such as saying, "Stand Clear. You're clear. I'm clear. We're all clear", then pressing the shock button when the first rescuer has made sure that no one is touching the patient. This process can cause for period of no delivery of therapeutic compressions for 5-10 seconds (e.g., the time lapse between cessation of chest compressions until the delivery of the electromagnetic energy can be 5-10 seconds). With the automatic detection of the rescuer proximity to the patient, the first rescuer arms the defibrillator, and then the second rescuer who has their hands on the sensor housing 104, delivering the compressions, actually causes the defibrillator to deliver the defibrillation shock by simply lifting their hands from off the sensor. Thus, the electromagnetic energy is automatically delivered upon detection of the removal of the rescuer's hands from the patient. This is believed to be particularly effective because the only person who will be in contact with the patient is the compressor at that point, and they are in the best position to assess whether anyone else might be in contact. When the rescuer lifts their hands off the sensor housing 104, the proximity sensor 216 detects that the rescuers hands have been removed from proximity of the patient and then automatically delivers the shock.

In some embodiments, E-field sensing such as that provided by the MC33941 (Freescale Semiconductor, document Number: MC33941, Rev 4) can be used (e.g., as shown in FIG. 8). Because this method of proximity sensing is fundamentally a measure of stray capacitance embodied by the rescuer's hands, it is important to calibrate to each rescuer because of the variable capacitance interjected by the use of medical gloves, etc. Calibration is accomplished automatically during the time that compressions are occurring. Because the sensor housing is being depressed during compressions, it can be safely assumed, particularly at the time when compression is at its deepest point, that the rescuer hands are in direct contact with the surface of the sensor housing 104. The measured capacitance at that point is taken as the zero-distance reference point.

There are additional benefits beyond minimizing the compression pauses during defibrillation. For instance, it is believed that synchronizing the defibrillation shock to the early phase of the compression upstroke significantly improves shock efficacy. By shocking immediately after detection of loss of rescuer hand contact, the defibrillation shock can be timed to the optimal phase of the compression cycle.

In some additional embodiments, rather than delivering the defibrillation shock immediately upon detection of removal of the rescuer's hands from the patient, one to ten EPS pulses may also be delivered immediately prior to the defibrillation shock, after the proximity sensor 216 and processor have detected loss of contact with the rescuer's hands. The defibrillation shock is then synchronized to the optimal phase of the final EPS pulse.

Alternatives to the E-field proximity sensor 216 are ultrasonic sensors such as the MINI_A PB Ultrasonic transducer (SensComp, MI) that has a measurement range of 1-12 inches. Alternatively, a light emitter-receiver pair may be located on the rescuer-facing upper surface of the sensor housing 104 and be used to detect the instant there is a physical separation between surface of the sensor housing 104 and the rescuer's hands.

Figure 4:
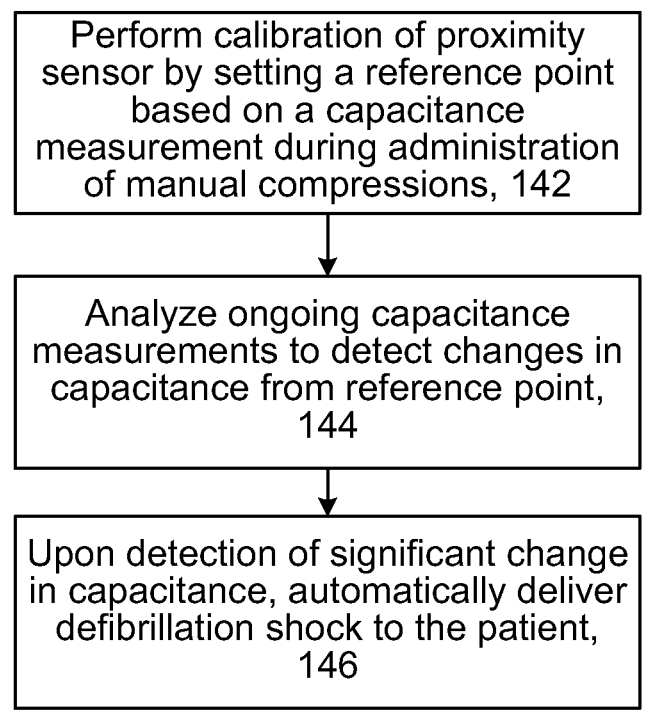
FIG. 4 is a flow chart of a method for detecting and using a rescuer's proximity to determine when to deliver a defibrillation shock.

FIG. 4 is a flow chart of a method for automatically delivering a defibrillation shock based on the detection of the removal of a rescuer's hands from a patient. The system performs a calibration of a proximity sensor by setting a reference point based on a capacitance measurement when compressions are being administered (142). The system analyzes ongoing capacitance measurements to detect changes in capacitance from reference point (144). Upon detection of significant change in capacitance (e.g., a change indicative of removal of the rescuer's hands from the patient), the system automatically delivers a defibrillation shock to the patient (146).

As discussed herein, in some embodiments, electrical stimulation can be used to cause blood flow in a patient similar to manual chest compressions to supplement manual delivery of manual chest compressions during periods of rescuer fatigue or cessation of chest compression delivery. In some embodiments, the electrical stimulation can include a two-stage electrical stimulation configured to electrically initiate blood flow based on the cardiac pump mechanism and the thoracic pump mechanism that are believed to be the two primary mechanisms for generation of blood flow during chest compressions in cardiopulmonary resuscitation (CPR). The two-stage electrical stimulation uses two sets of electrodes with a first set of electrodes located to stimulate muscle groups that during contraction produce blood flow primarily via the cardiac pump mechanism and a second set of electrodes located to stimulate muscle groups that during contraction produce blood flow primarily via the thoracic pump mechanism.

As the location of the electrode 101a is positioned so as to deliver EPS whose mechanism of blood flow is primarily via the so-called cardiac pump mechanism, it is optimal to also provide for additional EPS electrode locations that primarily stimulate thoracic muscles that, when contracting, will generate blood flow primarily via the so-called thoracic pump mechanism. Preferably, this location at on the left and right sides of the patient at the bottom of the rib cage. Anatomically speaking, the electrodes are positioned laterally, centered along the patient's anterior axillary line, and positioned vertically, centered on the costal margin of the $10^{th}$ rib. In this manner, the EPS stimulation is focused on the external oblique and the transversus abdominus muscles, thus causing a rapid reduction in both the transverse thoracic diameter (side-to-side width) and the sagittal thoracic diameter (front to back spacing between spine and front of rib cage), causing, in term, a rapid increase in the intrathoracic pressure. These we term the positive pressure thoracic pump EPS (PPTP-EPS) electrodes, because they generate primarily positive intrathoracic pressures during stimulation. The electrode position of electrode 101a and 101b we term the positive pressure cardiac pump EPS (PPCP-EPS) electrode position.

The stimulation pulses of the PPCP-EPS and PPTP-EPS electrodes may be coordinated (e.g., by an electronic controller) so that the two pulses coordinate their hemodynamic action to optimize blood flow. For instance, by delivering the PPCP-EPS pulse first, then pausing for 100-500 milliseconds, and optimally 100-200 milliseconds, then blood will be ejected from the heart and the aortic valve will be given sufficient time to close prior to delivery of the PPTP-EPS pulse that elevates intrathoracic pressure, and causes heightened aortic pressure. Since the aortic valve is more likely to be closed at this point because of the optimal inter-pulse timing, then the elevated aortic pressure will result in forward blood flow, as opposed to retrograde flow back into the left ventricle had the aortic valve been open.

In some embodiments, it can be beneficial to stimulate inhalation in a patient to provide oxygen to the patient while enabling the rescuer to continue to administer chest compressions. One method for electrically stimulating inhalation is by the stimulation of the intercostal muscles as a means of generating negative intrathoracic pressures to cause inspiratory ventilatory action. However, this method is believed to be unreliable. Thus, in order to provide a more reliable ventilatory action, electrical stimulations can be provided to promote sternocostal inhalation by stimulating one set of muscles that attach to some portion of the ribs, and by stimulating a second set of muscles that when contracted cause an opposing motion of the spine in either the sagittal or transverse axis.

More particularly, inhalation may be accomplished by two different sets of muscle action. The primary mechanism for most people is the contraction of the diaphragm, which increases the volume of the thoracic cavity, thus decreasing the intrathoracic pressure and the intake of air. Alternatively, a secondary means of increasing the volume of the thoracic cavity is by means of so-called sterno-costal breathing, sometimes also called costal or chest breathing. This breathing mode is often used during exercise or other anaerobic activity as a means of augmenting normal respiratory tidal volumes. Thoracic volume increase occurs by the general lifting of the ribs to increase either or both the transverse thoracic diameter or the sagittal thoracic diameter by the hinging action of the ribs on the vertebral bodies of the spine, specifically at the points of the costal tubercle and the head of the rib.

Prior art has described the stimulation of the intercostal muscles as a means of generating negative intrathoracic pressures to cause inspiratory ventilatory action. This is believed to be a highly unreliable as a mechanism, as the contraction of the intracostal muscles is as likely to pull down the superior ribs closer to the neck as it is to pull up the inferior ribs closer to the diaphragm. Unfortunately, pulling down the superior ribs actually causes elevated intrathoracic pressure and an exhalation, the opposite of what was intended.

Figure 5:
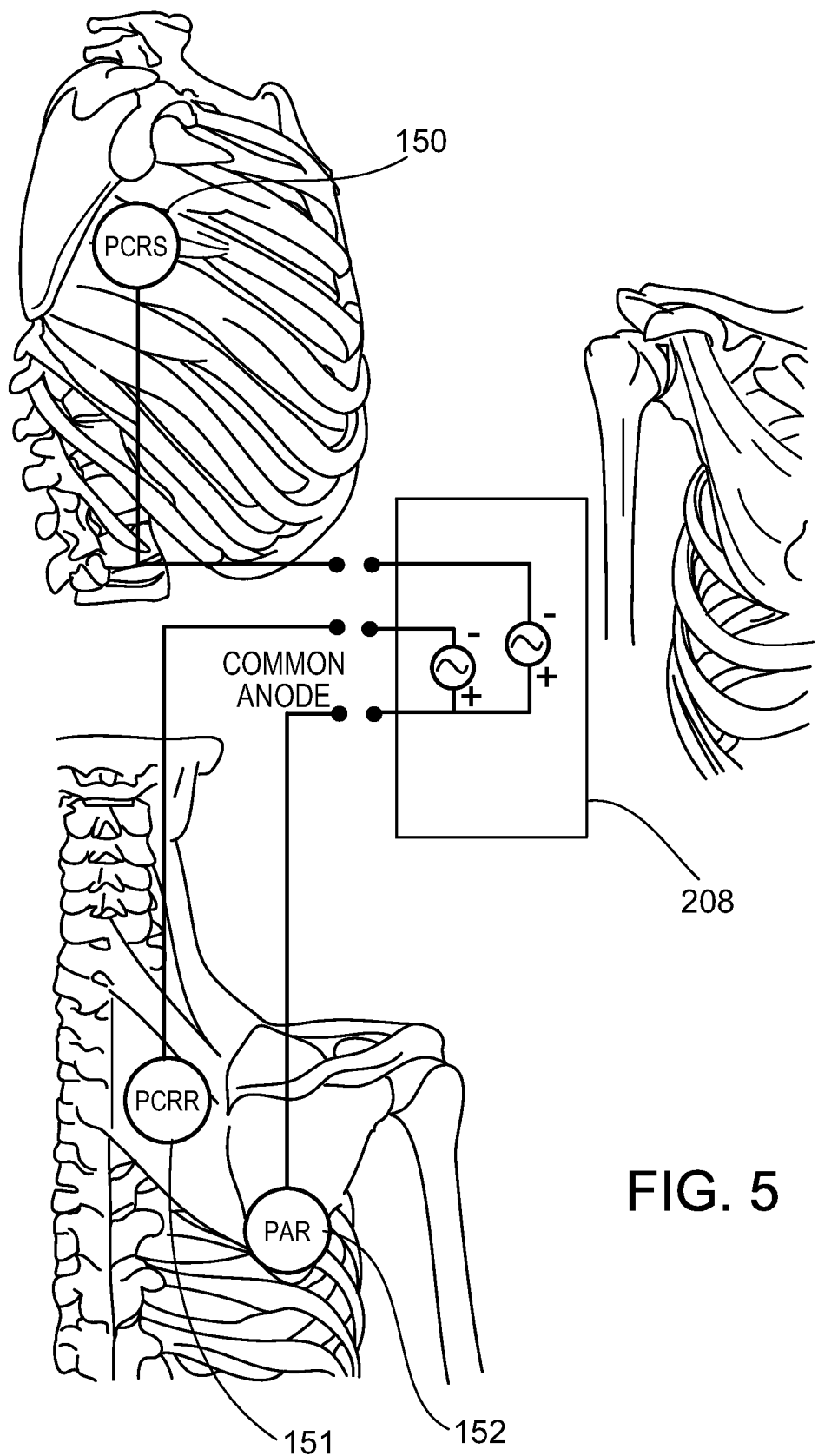
FIG. 5 shows the electrode placement for stimulation to enhance thoracic volume.

It has been discovered that by stimulating more than one muscle group in particular combinations and in a time-coordinated fashion, that rib cage can be elevated to effectuate sterno-costal breathing. As shown in FIG. 5, the sterno-costal breathing is promoted by multiple sets of electrodes (e.g., 150, 151, and 152) placed on the patient's skin. The electrodes can be controlled by control circuitry included in the defibrillator 208. These electrodes also act as negative pressure thoracic pump (NPTP) mechanism on hemodynamics. In one configuration, anodal electrodes approximately 2 inches in diameter are placed directly above the scapula with the circumference of the electrode approximately coincident with the inferior angle of the scapula. Each anode (posterior anode left [PAL] and posterior anode right [PAR] 152) is paired with two cathodal electrodes of approximately 2 inches in diameter: the first cathodal electrode is placed above the rhomboid major muscle (posterior cathode left rhomboid [PCLR] and posterior cathode right rhomboid [PCRR] 151), and the second cathodal electrode is placed above the serratus anterior muscle centered vertically at approximately the fifth or sixth rib (posterior cathode left serratus [PCLS] and posterior cathode right serratus [PCRS] 150). Electrodes are located on the left side of the posterior of the patient mirror those placed on the right in the figure. Bi-lateral stimulation of the rhomboid major muscles first before the serratus anterior muscles will cause the scapulae to be pinned to the spine, following which bi-lateral stimulation of the serratus will cause increase in the transverse thoracic diameter increase, intra-thoracic volume increase, intra-thoracic pressure decrease and sternocostal breathing. While it is preferable for the rhomboid muscles to be stimulated first, this is not an essential element and the method will still work with stimulation of the serratus anterior muscles first or simultaneously.

In general, this method of sternocostal inhalation via EPS works by stimulating one set of muscles that attach to some portion of the ribs, and by stimulating a second set of muscles that when contracted cause an opposing motion of the spine in either the sagittal or transverse axis. Another approach is to place the anodes in the right and left underarm or on the scapula as before, with cathodes placed just inferior to coracoid processes and along the spine above the trapezius. Cathodal stimulation of the trapezius causes arching of the back, then stimulation of the electrodes placed by the coracoid processes stimulate the pectoralis minor, teres major and latissimus dorsi to some extant to cause the ribs to rise primarily to increase the sagittal thoracic diameter.

Because these NPTP electrodes that are used for increasing thoracic volume are located primarily posterior, there is no risk of the currents generated during stimulation affecting the rescuer touching the patient. In particular, the benefit is that now the stimulation may be easily interposed with the rescuer's manual compressions. Triggering of the NPTP electrode stimulation is preferably timed to occur during the upstroke of the manual compression and will assist with returning the thorax to its natural configuration prior to the next manual compression downstroke as well as increase venous return into the atria to improve pre-load hemodynamics.

Figure 6:
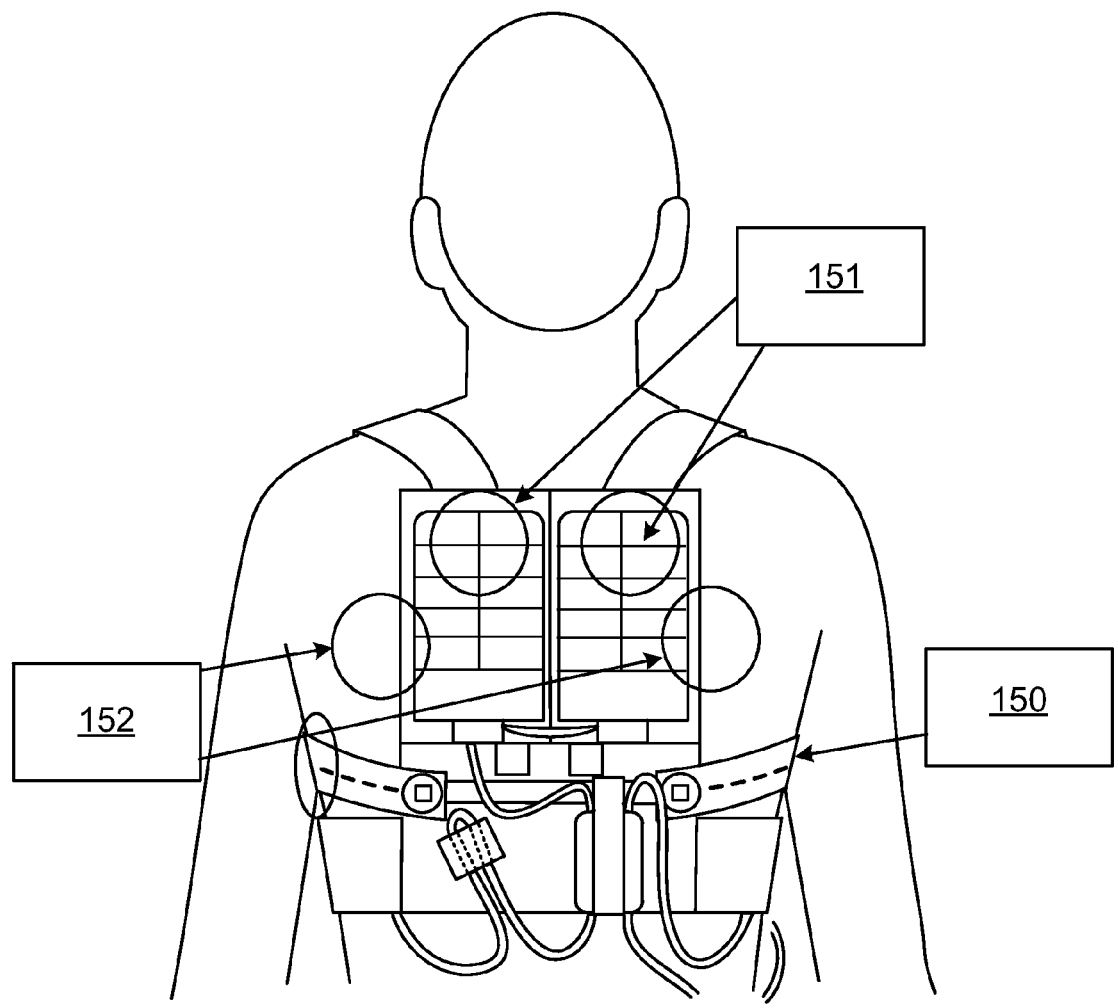
FIG. 6 shows placement of the electrode within a wearable defibrillator harness.

The EPS electrodes can be incorporated into the harness of a wearable defibrillator system such as the LIFEVEST® manufactured by ZOLL Medical (Chelmsford, Mass.). The EPS electrodes. For example, FIG. 6 shows an exemplary placement of the electrodes 150, 151, and 152 within a wearable defibrillator harness.

The three types of EPS pulses for PPCP, PPTP and NPTP may also be combined, either sequentially or simultaneously to enhance hemodynamics and generate better flow. For instance, a PPCP pulse may be followed by a PPTP pulse followed by a NPTP.

The EPS stimulating waveform itself may be modulated either by pulse width modulating the train of pulses or providing a ramped leading edge to create a more gentle ventilatory cycle for bringing air into the lungs. This will lessen the absolute instantaneous value of the intrathoracic pressure that may be desirous when attempting ventilation as opposed to trying to generate high peak intrathoracic pressures (either positive or negative) for enhanced movement of blood. More specifically, the stimulation is a series of high frequency pulses that may be delivered by the same circuitry that is used for defibrillation, such circuitry being known to those skilled in the art: a capacitor that is capable of storing voltages of up to 2000-4000 Volts; a charging circuit for charging such a capacitor, typically using a flyback transformer arrangement; a high voltage, high-speed solid-state switching mechanism for connecting the charged capacitor to a patient via a current carrying cable and patient-attached self-adhesive defibrillation electrodes. The just-mentioned switching mechanism is typically arranged to provide connection of the capacitor to the patient in both polarities, and is often configured as the classical H-bridge electrical switching network topology.

During EPS stimulation, the charging circuit maintains the voltage on the capacitor to a desired voltage, typically on the order of 500 Volts. The H-bridge circuit may be controlled to deliver either a monophasic or biphasic pulse train, though preferably the pulse train is monophasic. The pulses may be pulse-width modulated to deliver a pulse train with the leading edge of the pulse train with a duty cycle of as little as 0.1%, and ramping up to a duty cycle of that which is sustained through the remainder of the EPS stimulation. The sustained duty cycle for the EPS stimulation at the conclusion of the ramp may be a duty cycle of as little as 0.1% to as much as 100% (i.e. DC). The effective DC value of the waveform during the ramp portion of the stimulation may have a linear shape, or may be more complex, taking the form of an exponential or logarithmic or an arbitrary polynomial. The sustained duty cycle for the EPS stimulation at the conclusion of the ramp may vary over the time course of the interval during which EPS stimulation is being delivered, since muscle fatigue occurs during the typically 30 seconds of EPS stimulation. For instance, if the maximum duration for EPS stimulation is set for 30 seconds, the sustained duty cycle might be start at 10% for the first 10 seconds of the seconds then increasing gradually to 30% over the course of the remaining 20 seconds.

The individual 100-200 microsecond pulses may be delivered as biphasic pulse pairs. Since nerves and muscles respond to the average voltage of the pulse pairs, the average voltage can be ramped by fixing voltage of the positive and negative voltages and achieving a zero average voltage with equal duration positive and negative 100 microsecond pulses. While pulses are preferably 100-200 microseconds, they may be as short as 5 microseconds or as long as 10 milliseconds for multipulse pulse trains and as long as 200 milliseconds for single pulse stimulation.

The timing of the EPS stimulations may also be coordinated with an ECG waveform so that such motions do not occur during the vulnerable period of the cardiac cycle or are minimized during such period. For example, the defibrillator may be controlled so as to not start a stimulation until after the vulnerable period has passed, or can be synchronized to the R-wave of the ECG but reduce the duration of the stimulation so that the compression upstroke does not overlap the vulnerable T-wave. Second, the EPS waveform may also be modulated to reduce the velocities of the thoracic cage as higher velocities may result in re-induction of ventricular fibrillation, particular immediately after the defibrillation shock and then gradually increase the forcefulness of the stimulation closer to the start of a next shock. In this manner, blood circulation may be maximized by providing greater pumping power at the end of a shocking cycle (and also thereby increasing the effectiveness of the next shock), while minimizing the interference with the heart at the beginning of the cycle when the heart is more vulnerable.

FIG. 7 shows an example system 200, in schematic form, for providing dynamically controlled chest compression to a patient. In general, the system 200 involves a number of medical devices that may be used to provide life-saving care to a victim, such as a victim 202, of sudden cardiac arrest. The various devices may be part of a single unit or multiple units, and may be used to monitor various real-time physical parameters of the victim 202, to communicate between the components and with remote systems such as central caregivers, and to provide care to the victim 202 or provide instructions to caregivers, such as caregiver 204, in providing care to the victim 202.

The victim 202 in this example is an individual who has apparently undergone sudden cardiac arrest is being treated by the caregiver 204. The caregiver 204 may be, for example, a civilian responder who has had limited training in lifesaving techniques, an emergency medical technician (EMT), a physician, or another medical professional. The caregiver 204 in this example may be acting alone or may be acting with assistance from one or more other caregivers, such as a partner EMT.

The victim 202 is in a position in which therapy has been provided to the victim 202. For example, a set of defibrillator electrodes have been applied to the victim's torso in a typical manner and are in wired connection to a portable external defibrillator 208. The defibrillator 208 may be, for example, a typical automated external defibrillator (AED), a professional defibrillator, or other similar type of defibrillating apparatus. The victim 202 has also been provided with a ventilation bag (not shown), to provide forced air into the victim's longs to assist in rescue breathing of the victim 202. The defibrillator 208 and ventilation bag may be operated in familiar manners and in coordination by various caregivers. Also, the ventilation bag may be fitted with various sensors and transmitters so as to communicate electronically with the defibrillator 208. For example, a volumetric flow sensor may be provided with the ventilation bag, and data about the volume of airflow to and from the victim may be passed to defibrillator 208, so the defibrillator 208 may relay such information, or may also use such information to affect the manner in which defibrillation is provided to the victim 202.

A computer tablet 214 is also shown communicating with the other devices, and being manipulated by caregiver 204. The tablet may serve as a general electronic command post for the caregiver 204 to receive information about the victim 202 and other items, to communicate with other caregivers, and to provide input in controlling the operation of the various components in the system 200. The tablet 214 may be provided with short range and long range wireless communication capabilities, such as BLUETOOTH® or WiFi® on the one hand, and cellular 3G or 4G on the other. The caregiver 204 may input information into the tablet computer 214, such as information describing the condition of the victim 202 and other similar information that is to be recognized and recorded by the caregiver 204. The tablet 214 may also be in data communication with multiple sensors for sensing real-time information about the victim 202, such as blood pressure, pulse, and similar real-time patient parameters. The caregiver 204 may also input information into tablet 214 so as to control one or more of the medical devices being used with the victim 202. For example, the user may adjust the type, intensity, speed, or coordination of treatment that is provided to the victim 202.

Chest compression are delivered manually by the Caregiver 204. In such a case, audiovisual feedback is provided to the Caregiver 204 via Speaker 236*a* and Display 224. Feedback will direct the Caregiver 204 to deliver compressions 218 less forcefully when necessary.

As shown in this example, multiple different input signals are received that characterize the current real-time condition or physical parameters of the victim 202. For example, an ECG signal 222 may be received by the MPU 212 and may represent current and real time ECG waveforms for the victim 202, which may be obtained by leads connected to defibrillator 208.

An SpO$_2$ signal 224, or other physiologically-derived signal that is either a direct or indirect measure of circulatory flow or perfusion, is also captured at SpO$_2$ signal box 224, and may be used to further determine when and at what force to apply chest compressions to the victim 202.

Note that while FIG. 7 shows specific examples of input signals such as SpO2, an apparatus could use any combination of physiological signals such as, but not limited to: ECG; measures of cardiac output; measures of heart rate; blood pressure(s); oxygen saturation (SpO2); heart sounds (including phonocardiography); heart imaging (including ultrasound); impedance cardiography. Compression parameters could use any combination of features or measurements of compression including, but not limited to: compression velocity; compression depth; duty cycle; velocity of downstroke and upstroke; intrathoracic pressures during compressions; pleural pressures during compressions; sternal position, velocity or acceleration; chest wall or sternal strain or deformation; force applied to the chest; pressure used to compress the chest by a mechanical chest compressor.

A signal processing unit 228 is provided to filter inputs, such as ECG inputs, received from the patient for further analysis by the Microprocessor 230. For example, the signal processing unit 228 may filter noise from input signals, and in the case of ECG data may filter artifacts created by chest compression motion 226 of the victim 202 in order to remove such artifacts. Such preparation of ECG signals may be termed SEE-THRU CPR, and can be performed as discussed in U.S. Pat. No. 6,865,413, filed Jan. 23, 2002, and entitled ECG SIGNAL PROCESSOR AND METHOD, the teachings of which are incorporated herein by reference in their entirety.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

The computer system may include software for implementing an electronic patient care record, for example the ePCR software of ZOLL Data Systems (Broomfield Colo.). The software provides the ability to enter, store and transmit patient information as well as therapeutic interactions. The computer is often a so-called "Tablet" computer system that has been ruggedized for pre-hospital use, but may also take the form of an iPhone or iPad. Data is preferably transmitted in real time between the portable "Tablet" computer 214 to the MPU 212.

Electromagnetic stimulation may be accomplished via electrical stimulation such as current source or a voltage source known to those skilled in the art for use as pacing or defibrillation circuitry. Electromagnetic stimulation may also be accomplished by magnetic stimulation accomplished by high current pulses, typically 10 Amps or more, delivered into magnetic coils placed closed to the muscle groups needing to be stimulated. Such systems have been available commercially by Cadwell Inc (Device model MES-10).

A number of embodiments have been described. Nevertheless, it will be understood that various modifications may be made without departing from the spirit and scope of the invention. Accordingly, other embodiments are within the scope of the following claims.

What is claimed is:

1. A medical system for providing electromagnetic stimulation of a patient, comprising:
   a sensor positioned to sense the presence of manual chest compressions administered to the patient by a rescuer;
   a processor arranged to receive data generated by the sensor and detect changes in the administration of the chest compressions; and
   circuitry configured for delivery of electromagnetic stimulation to the patient to stimulate blood flow in the patient upon detection of a change comprising a degradation in quality in the administration of the chest compressions.

2. The system of claim 1, wherein the degradation in quality of the chest compressions comprises a change in depth of the chest compressions.

3. The system of claim 1, wherein the degradation in the quality of the chest compressions comprises a change in compression release of the chest compressions.

4. The system of claim 1, wherein the processor is configured to detect changes in the administration of the chest compressions by detecting an absence of chest compressions for a period of time greater than a threshold.

5. The system of claim 1, wherein the processor is configured to detect changes in the administration of the chest compressions by detecting an absence of chest compressions for a period of time greater than 2 seconds.

6. The system of claim 1, wherein the processor is configured to detect changes in the administration of the chest compressions by comparing data generated by the sensor during a first time period with data generated by the sensor during a second time period that occurs after the first time period.

7. The system of claim 1, wherein the sensor is configured to detect motion of the patient's sternum.

8. The system of claim 1, wherein the sensor comprises a motion sensor.

9. The system of claim 1, wherein the sensor comprises a pressure sensor.

10. The system of claim 1, wherein the sensor comprises a velocity sensor.

11. The system of claim 1, wherein the circuitry configured for delivery of electromagnetic stimulation is further configured to deliver the electromagnetic stimulation automatically and without user intervention.

12. The system of claim 1, wherein the circuitry configured for delivery of electromagnetic stimulation comprises an electrode assembly affixed to the patient's thorax.

13. The system of claim 12, wherein the electrode assembly is removably affixed to the patient's thorax.

14. The system of claim 1, wherein the circuitry comprises circuitry configured to deliver a pulse packet of 100-200 microsecond duration pulses with inter-pulse spacing of 5-15 milliseconds and an amplitude of 300-700 volts.

15. The system of claim 1, wherein the circuitry comprises circuitry configured to deliver a pulse packet of 20-1000 microsecond duration pulses with a duty cycle of 2-95% and an amplitude of 50-2000 volts.

16. The system of claim 1, further comprising a display device configured to visually prompt the rescuer to resume manual chest compressions upon initiation of delivery of the electromagnetic stimulation to the patient.

17. The system of claim 1, further comprising a speaker configured to provide an audio prompt the rescuer to resume manual chest compressions upon initiation of delivery of the electromagnetic stimulation to the patient.

18. The system of claim 1, wherein the processor is configured to detect changes in the administration of the chest compressions by detecting a degradation in the quality of chest compressions.

19. The system of claim 18, wherein the circuitry is configured to deliver the electromagnetic stimulation simultaneously with the administration of the manual chest compressions by the rescuer upon detection of the degradation in the quality of chest compressions.

20. The system of claim 1, wherein the processor is arranged to detect the degradation in the quality of the chest compressions based, at least in part, on one or more of change point analysis and Shewhart control charts.

21. The system of claim 1, wherein detection of the degradation in the quality of the chest compressions comprises detection of a compression depth of less than 2 inches.

22. The system of claim 1, wherein detection of the degradation in the quality of the chest compressions comprises detection of a compression rate of slower than one compression every 600 milliseconds.

\* \* \* \* \*